United States Patent
Tyler et al.

(10) Patent No.: US 8,219,415 B2
(45) Date of Patent: Jul. 10, 2012

(54) CHARACTERIZING RELATIONSHIPS AMONG PROCEDURES USING SIMILARITY METRICS

(75) Inventors: Michael Tyler, San Diego, CA (US); Moiz Saifee, Ujjain (IN); Nitin Basant, Ramgarh Cant (IN); Shafi Rahman, Bangalore (IN)

(73) Assignee: Fair Isaac Corporation, Minneapolis, MN (US)

( * ) Notice: Subject to any disclaimer, the term of this patent is extended or adjusted under 35 U.S.C. 154(b) by 604 days.

(21) Appl. No.: 12/057,243

(22) Filed: Mar. 27, 2008

(65) Prior Publication Data

US 2009/0248438 A1    Oct. 1, 2009

(51) Int. Cl.
*G06Q 10/00* (2006.01)
(52) U.S. Cl. .................... 705/2; 705/1; 705/3
(58) Field of Classification Search ........ 705/2
See application file for complete search history.

(56) References Cited

U.S. PATENT DOCUMENTS

| | | | |
|---|---|---|---|
| 6,253,102 B1* | 6/2001 | Hsu et al. | 600/515 |
| 6,915,254 B1* | 7/2005 | Heinze et al. | 704/9 |
| 7,136,852 B1* | 11/2006 | Sterling et al. | 1/1 |

* cited by examiner

*Primary Examiner* — Hiep V Nguyen
(74) *Attorney, Agent, or Firm* — Mintz, Levin, Cohn, Ferris, Glovsky and Popeo, P.C.

(57) ABSTRACT

Data is received that characterizes a plurality of procedures for a single event. Thereafter, one or more dynamically determined groups are associated with the plurality of procedures, the dynamically determined groups being generated from similarity metrics derived from a plurality of historical procedures for a plurality of historical events. A likelihood of the plurality of procedures being associated with the single event can then be determined based on the associated one or more dynamically determined groups. This determined likelihood can be used to determine whether the data is indicative of fraud. Related apparatus, systems, techniques and articles are also described.

19 Claims, 2 Drawing Sheets

CHARACTERIZING RELATIONSHIPS AMONG PROCEDURES USING SIMILARITY METRICS

BACKGROUND

Healthcare fraud continues to be a growing problem in the United States and abroad. According to the Centers for Medicare and Medicaid Services (CMS), fraud schemes range from those perpetrated by individuals acting alone to broad-based activities by institutions or groups of individuals, sometimes employing sophisticated telemarketing and other promotional techniques to lure consumers into serving as the unwitting tools in the schemes. Seldom do perpetrators target only one insurer or either the public or private sector exclusively. Rather, most are found to be simultaneously defrauding public sector victims such as Medicare and private sector victims simultaneously.

CMS reports that annual healthcare expenditures in the United States totaled over $2 trillion dollars in 2006, and at that time were expected to increase 6.5% a year. Though the amount lost to healthcare fraud and abuse cannot be precisely quantified, the general consensus is that a significant percentage is paid to fraudulent or abusive claims. Many private insurers estimate the proportion of healthcare dollars lost to fraud to be in the range of 3-5%. It is widely accepted that losses due to fraud and abuse are an enormous drain on both the public and private healthcare systems.

Medical providers use a standardized system of numerical codes for patient services that are required by government programs such as Medicare and Medicaid. This way insurers and the government do not have to decipher what services were provided from thousands of different types of coding or billing systems. There are several codes that are applicable for medical procedures. The misuse of these standardized codes to obtain more money than the provider would otherwise be entitled to is commonly termed "upcoding". Each medical procedure code corresponds to a particular service and will eventually result in reimbursement to the physician or other provider based upon the code entered. Providers or the organization they work for have financial incentives to increase the bill by exaggerating or even falsely representing what medical conditions were present and what services were provided.

An example of upcoding would be when a patient receives a two-minute visit for the treatment of an upper respiratory condition, but is charged for a longer visit that would indicate a more serious condition. The provider may bill for a one hour visit, even though the provider saw the patient for a very short time. In some cases, the diagnosis may be altered to falsely diagnose the patient suffering from a more severe condition. If the provider bills for a procedure that indicate a higher level of service than the patient received, fraud has occurred.

One of the main problems in detecting upcoding is that there are a large number of procedure codes (>10,000). Deciding which codes have the potential to be upcoded, and which codes they can upcoded towards, has been a manually intensive process in the past.

SUMMARY

In one aspect, data is received that characterizes a plurality of procedures for a single event. Thereafter, one or more dynamically determined groups are associated with the plurality of procedures, the dynamically determined groups being generated from similarity metrics derived from a plurality of historical procedures for a plurality of historical events. A likelihood of the plurality of procedures being associated with the single event can then be determined based on the associated one or more pre-determined groups. These procedure groups can then be used to search for various aspects of fraud, including upcoding.

The historical procedures can be grouped, for example, pairwise disjoint into a set of dynamically determined groups. In other variations, procedures may belong to more than one group.

Various techniques may be used to identify the procedures including, for example, codes, short descriptions, and the like. In implementations relating to healthcare, the single event can comprise a plurality of healthcare procedures identified as being related to a single medical condition or hospital or doctor's office visit, etc.

The similarity metrics can be determined, for example, using this or a similar metric:

$$s = \frac{N(P_1, P_2)}{N(P_1) * N(P_2)}$$

where,
s=similarity metric;
$N(P_1, P_2)$=number of characteristics shared by Procedures $P_1$ and $P_2$;
$N(P_1)$=number of characteristics that were associated with $P_1$ in historical data; and
$N(P_2)$=number of characteristics that were associated with $P_2$ in historical data.

The characteristics used to calculate a similarity metric can include, for example, the occurrence of diagnosis codes, a procedure description, as being related to a single series of medical procedures place of service, and the like. As an alternative or in combination with the similarity metric equation described above, the similarity metrics can be determined based on a distance between two context vectors where each context vector characterizes one or more attributes of a procedure.

The plurality of historical procedures can be hierarchically clustered based on similarity metrics for each pair of historical procedures. These hierarchical clusters can be used to find sets of related procedure codes. These codes can then be used in provider profiling and peer comparisons, to search for upcoding, and a variety of other techniques to detect provider fraud.

Notification can be initiated if it is determined that the likelihood of the procedures being associated with the single event is below a pre-determined level. The notification can identify the single event as containing procedures that are indicative of fraud or error (e.g., if some or all of the procedures are not related according to the similarity metrics, etc.). The notification can also specifically identify which procedures are indicative of fraud or error.

In an interrelated aspect, data characterizing a plurality of historical procedures associated with a plurality of historical events is received. Thereafter, similarity metrics are calculated for pairs of procedures (e.g., disjoint pairs of procedures, etc.). A plurality of groups of procedures based on the similarity metrics are then generated. Access to the generated plurality of groups of procedures can be provided to enable a determination to be made regarding a likelihood of future procedures being associated with a single event.

Articles are also described that comprise a machine-readable medium embodying instructions that when performed by one or more machines result in operations described herein.

Similarly, computer systems are also described that may include a processor and a memory coupled to the processor. The memory may encode one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
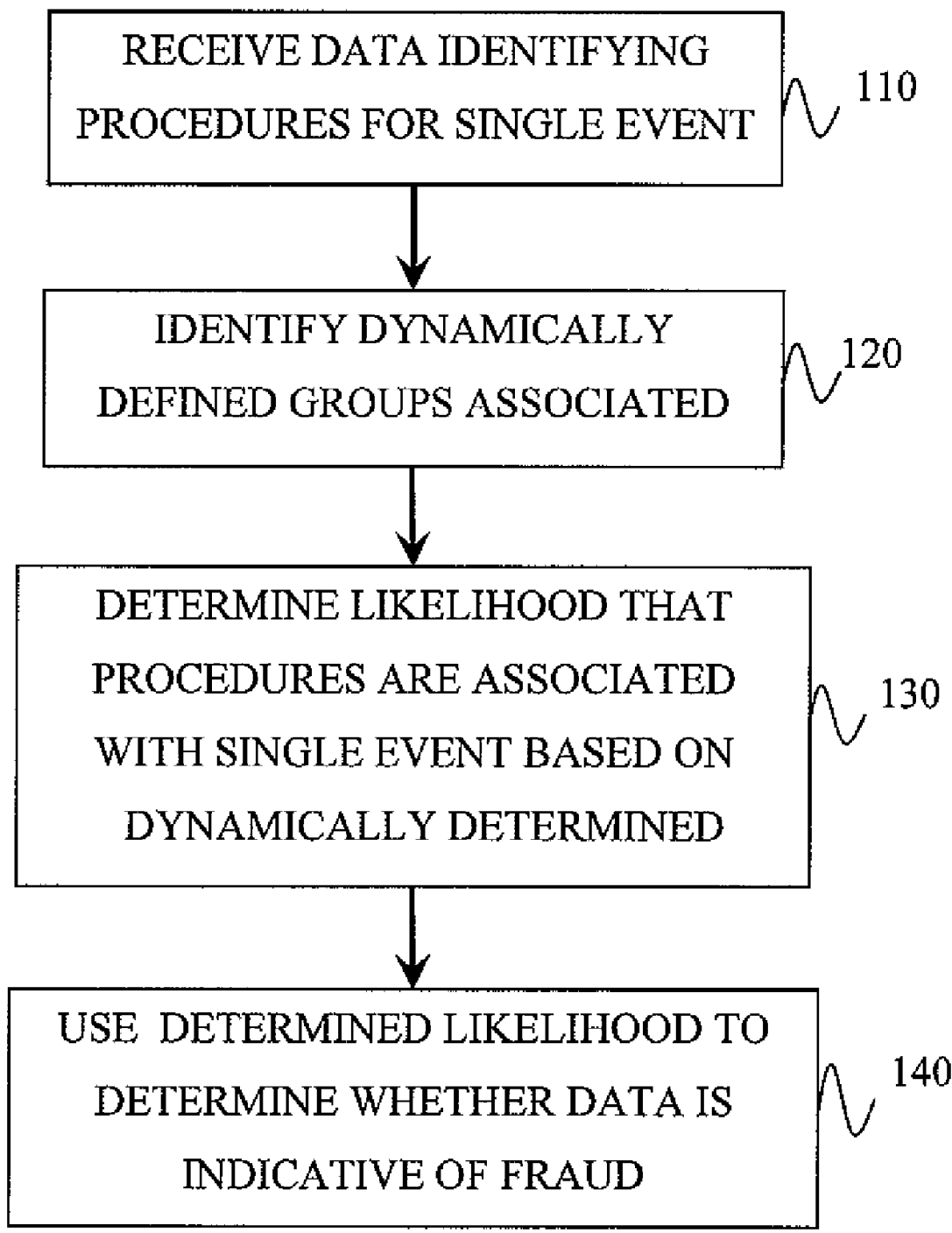
FIG. 1 is a process flow diagram illustrating a method for characterizing whether a likelihood of whether a plurality of procedures are associated with a single event.

FIG. 1 is a process flow diagram that illustrates a method 100, in which at 110, data characterizing a plurality of procedures for a single event is received. Thereafter, at 120, one or more dynamically determined groups associated with the plurality of procedures are identified. These groups can be generated from similarity metrics derived from a plurality of historical procedures for a plurality of historical events. A likelihood of the plurality of procedures being associated with the single event based on the associated one or more dynamically determined groups is, at 130, determined. Thereafter, at 140, a determination can be made whether the data is indicative of fraudulent activity based on the determined likelihood. Such a determination can be made using various fraud detection and/or profiling algorithms, and such a user can be alerted to such a determination.

Figure 2:
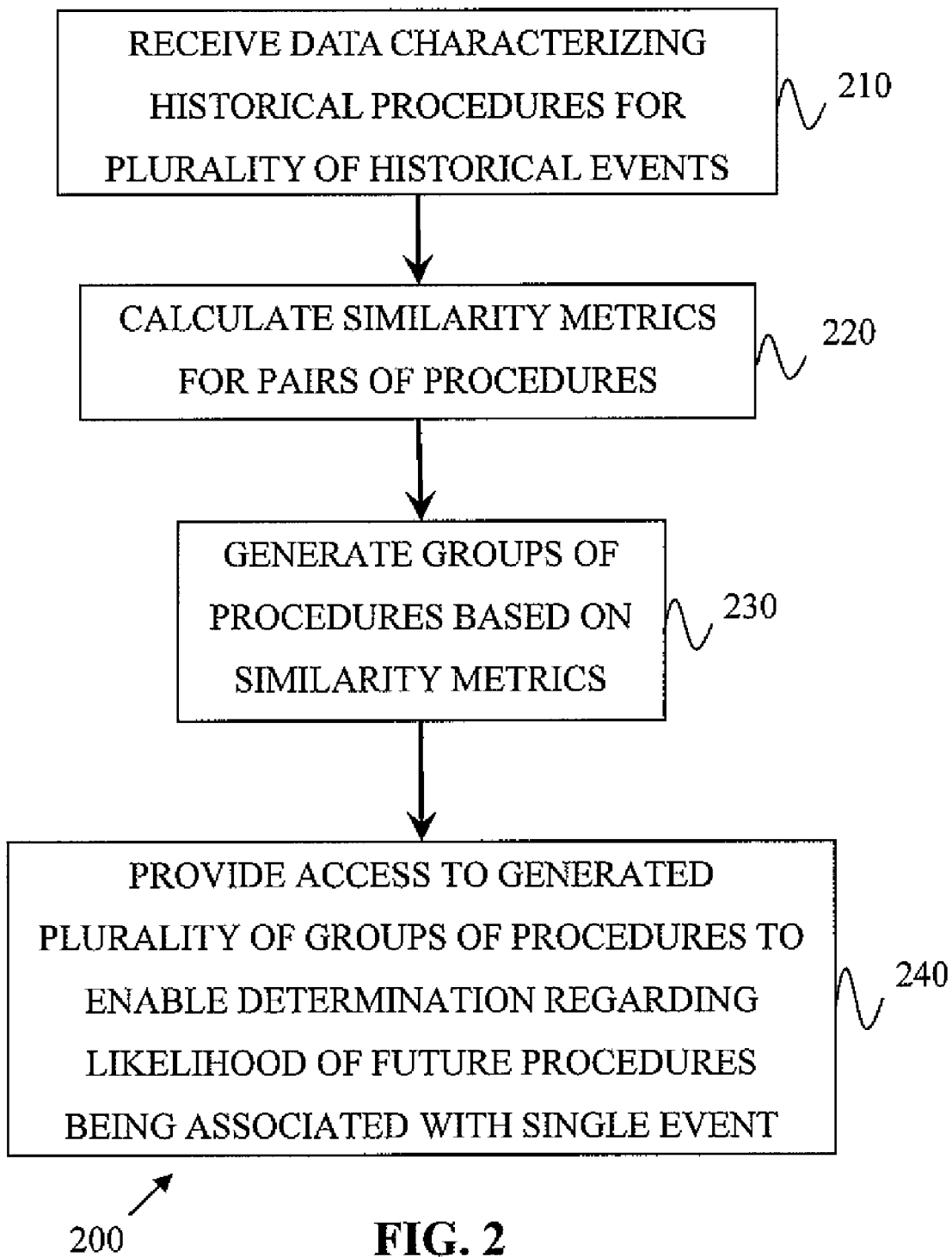
FIG. 2 is a process flow diagram illustrating a method for grouping historical procedures that are associated with a plurality of historical events to enable characterization of future procedures identified as being associated with a single event.

FIG. 2 is a process flow diagram, showing a method 200, interrelated to the method 100 of FIG. 1, in which, at 210, data characterizing a plurality of historical procedures associated with a plurality of historical events is received. Subsequently, at 220, similarity metrics are calculated for disjoint pairs of procedures so that, at 230, a plurality of groups of procedures based on the similarity metrics can be generated. Access can, at 140, be provided to the generated plurality of groups of procedures to enable a determination to be made regarding a likelihood of future procedures being associated with a single event.

The subject matter described herein provides methods, articles, and systems for performing a data driven grouping of procedures (or other types of event). While the following is described primarily in connection with medical procedures (and related codes), it will be appreciated that the current subject matter can be utilized in connection with any application in which it is useful to determine whether several procedures (or other acts) are likely to have been associated with a single type of event or whether the several procedures are likely to have been associated with multiple types of events.

By grouping medical procedures (which are identified by codes), procedures can be divided into categories which are clinically meaningful. These groups can then be used to catch systematic fraud such as upcoding. These groups can also be used to characterize and/or identify disease spells, generate provider profiles, generate consumer profiles, and identify other macro and micro trends.

The procedure grouping methodologies which have been utilized in the past are based on the clinical knowledge and are created manually. One disadvantage of the manual classification technique is the burden involved in regrouping the procedures whenever there is a change in procedure coding scheme. The manual grouping is a time intensive process requiring effort of someone with skills and knowledge of the medical coding system, and once the effort has been put forth to create the grouping, it is fixed. The advantage of the data driven grouping scheme described herein is that it takes historical data to quickly and automatically learn which procedures are related and categorize them into desired number of groups.

The grouping methodology described herein is very flexible in the sense that the user can specify the number of groups into which one wants to divide the procedures. When the grouping is very fine (the number of groups is very large), the procedures which fall within the same group are very similar, often interchangeable. Such a grouping can therefore be used to detect schemes such as upcoding. When the grouping is coarser (a relatively smaller number of groups), the groups contain more number of procedures which would be related through an illness or a body part. This type of grouping has applications in creating disease spells, or constructing provider or consumer profiles.

The grouping scheme does a hierarchical clustering of the procedure, based on a similarity metric for every pair of procedures, which signifies the strength of relationship between two procedures. The similarity metric can be computed in a variety of ways, all revolve around finding characteristics which tend to be similar or common for related procedures. Examples of such characteristics are diagnosis code, procedure description, place of service, etc. Pairs of procedures scoring high on the similarity metric tend to share a higher percentage of diagnosis code as compared to pairs of procedure codes scoring low on the similarity matrix.

A number of metrics can be computed that find similarity in either of these dimensions. Examples of similarity metric using diagnosis code and procedure description are described below, but there are many forms each of these components can take.

A similarity metric for a procedure code can, for example, be calculated using:

$$s = \frac{N(P_1, P_2)}{N(P_1) * N(P_2)}$$

Where,
s=Similarity Metric
$N(P_1, P_2)$ =Number of diagnosis codes shared by Procedures $P_1$ and $P_2$.
$N(P_1)$=Number of diagnosis codes that were associated with $P_1$ in historical data.
$N(P_2)$=Number of diagnosis codes that were associated with $P_2$ in historical data.

In addition to, or in lieu of the equation above, similarity metrics can be based on context vectors. In particular, context vectors can be evaluated for the procedure description and then Euclidian distance between context vectors of two sentences can be one of the parameters representing similarity of meaning of the descriptions and hence the procedure codes. The context vector technique for text representation uses a high dimensional vector to represent each word in the text data. Using a corpus of training text, frequently occurring "stop" words are dropped, words that occur in group are grouped together and "stems" of words are formed to eliminate duplication due to plurality, tense etc. A neural network based adaptive learning technique can then be used to assign vectors to each stem such that stems that occur together or are used in similar contexts have vectors pointing in same direction. Higher level object such as a sentence is then created in the same vector space by using normalized weighted sum of vectors of each stem.

For further techniques for generating and characterizing context vectors see, for example, U.S. Pat. No. 5,325,298 entitled "Method for Generating or Revising Context Vectors for a Plurality of Word Stems" and U.S. Pat. No. 7,251,637 entitled "Context Vector Generation and Retrieval", the contents of both are hereby fully incorporated by reference.

If multiple characteristics (e.g., diagnosis code and procedure description, etc.) and/or techniques (e.g., equation above, context vectors, etc.) are used for calculating a similarity metric, the resulting values can be combined into an overall similarity metric for two procedures. After this, hierarchical clustering of the procedures can be performed using the similarity metric values. The number of groups to be formed can be given as an input to the clustering algorithm.

The groups of procedures can then be used in any application in which it might be useful to characterize a likelihood of a plurality of procedures being associated with a single type of event such as medical insurance fraud detection and profiling activities.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein do not require the particular order shown, or sequential order, to achieve desirable results. Other embodiments may be within the scope of the following claims.

What is claimed is:

1. An article comprising a non-transitory machine-readable medium embodying instructions that when performed by one or more machines result in operations comprising:
   receiving data characterizing a plurality of procedures represented as being associated with a single event, the single event comprising a plurality of healthcare procedures performed on a patient that are all related to a single medical condition;
   identifying one or more dynamically determined groups associated with the plurality of procedures, the dynamically determined groups being generated from similarity metrics derived from a plurality of historical procedures for a plurality of historical events;
   determining a likelihood of the plurality of procedures being associated with the single event based on the associated one or more dynamically determined groups; and
   initiating notification if it is determined that the likelihood of the procedures being associated with the single event is below a dynamically determined level;
   wherein the similarity metrics are determined using:

$$s = N(P_1, P_2)/N(P_1)*N(P_2)$$

where,
s=similarity metric;
$N(P_1, P_2)$=number of characteristics shared by Procedures $P_1$ and $P_2$;
$N(P_1)$=number of characteristics that were associated with $P_1$ in historical data; and
$N(P_2)$=number of characteristics that were associated with $P_2$ in historical data.

2. An article as in claim 1, wherein the historical procedures are grouped pairwise into the dynamically determined groups.

3. An article as in claim 1, wherein the procedures are identifying using codes.

4. An article as in claim 1, wherein the characteristics are selected from a group comprising: diagnosis codes, procedure description, and place of service, type of service, data characterizing a performed service.

5. An article as in claim 1, wherein the similarity metrics are determined based on a distance between two context vectors, each context vector characterizing one or more attributes of a procedure.

6. An article as in claim 1, wherein an additional similarity metric is determined based on a distance between two context vectors, each characterizing one or more attributes of a procedure, and wherein two or more similarity metrics for each procedure pair is combined.

7. An article as in claim 1, wherein the plurality of historical procedures are hierarchically clustered based on similarity metrics for each pair of historical procedures.

8. An article as in claim 1, wherein the notification identifying the single event as containing procedures that are indicative of fraud or error.

9. An article as in claim 1, wherein the notification identifies which procedures are indicative of fraud or error.

10. An article as in claim 1, wherein at least one similarity metric is determined based on a Euclidean distance between two context vectors, each context vector characterizing one or more attributes of a procedure, and wherein two or more similarity metrics for each procedure pair is combined.

11. A method for implementation by one or more data processors comprising:

receiving, by at least one data processor, data characterizing a plurality of procedures represented as being associated with a single event, the single event comprising a plurality of healthcare procedures performed on a patient that are all related to a single medical condition;

identifying, by at least one data processor, one or more dynamically determined groups associated with the plurality of procedures, the dynamically determined groups being generated from similarity metrics derived from a plurality of historical procedures for a plurality of historical events; and determining, by at least one data processor, a likelihood of the plurality of procedures being associated with the single event based on the associated one or more dynamically determined groups;

wherein the similarity metrics are determined using:

$$s = N(P_1, P_2)/N(P_1)*N(P_2)$$

where, s=similarity metric;

$N(P_1, P_2)$=number of claims where Procedures $P_1$ and $P_2$ share a common code;

$N(P_1)$=number of claims that were associated with $P_1$ in historical data; and $N(P_2)$=number claims that were associated with $P_2$ in historical data.

12. A method as in claim 11, wherein the historical procedures are grouped pairwise into the dynamically determined groups.

13. A method as in claim 11, wherein the procedures are identified using codes.

14. A method as in claim 11, wherein the code is selected from a group comprising: diagnosis codes, procedure description, and place of service.

15. A method as in claim 11, wherein the notification identifying the single event as containing procedures that are indicative of fraud or error.

16. A method as in claim 11, wherein the notification identifies which procedures are indicative of fraud or error.

17. An article comprising a non-transitory machine-readable medium storing instructions that when performed by one or more machines result in operations comprising:

receiving data characterizing a plurality of historical procedures associated with a plurality of historical events, each historical event comprising a plurality of healthcare procedures performed on a patient that are all related to a single medical condition;

calculating similarity metrics for disjoint pairs of procedures;

generating a plurality of groups of procedures based on the similarity metrics, wherein a user can specify a level of coarseness of groupings of the groups of procedures; and providing access to the generated plurality of groups of procedures to enable a determination to be made regarding a likelihood of future procedures being associated with a single event;

wherein the similarity metrics are determined using:

$$s = N(P_1, P_2)/N(P_2)*N(P_2)$$

where, s=similarity metric;

$N(P_1, P_2)$=number of claims where Procedures $P_1$ and $P_2$ share a common code;

$N(P_1)$=number of claims that were associated with $P_1$ in historical data;

$N(P_2)$=number claims that were associated with $P_2$ in historical data.

18. An article as in claim 17, wherein the code is selected from a group comprising: diagnosis codes, procedure description, and place of service.

19. An article as in claim 17, wherein the similarity metrics are determined based on a distance between two context vectors, each context vector characterizing one or more attributes of a procedure.

* * * * *